(12) United States Patent
Yoshida

(10) Patent No.: US 8,716,501 B2
(45) Date of Patent: May 6, 2014

(54) METHOD FOR PRODUCING OXYGEN-CONTAINING COMPOUND

(75) Inventor: Masaaki Yoshida, Utsunomiya (JP)

(73) Assignee: Utsunomiya University, Tochigi (JP)

( * ) Notice: Subject to any disclaimer, the term of this patent is extended or adjusted under 35 U.S.C. 154(b) by 191 days.

(21) Appl. No.: 13/201,918

(22) PCT Filed: Feb. 17, 2010

(86) PCT No.: PCT/JP2010/052385
§ 371 (c)(1),
(2), (4) Date: Oct. 31, 2011

(87) PCT Pub. No.: WO2010/095669
PCT Pub. Date: Aug. 26, 2010

(65) Prior Publication Data
US 2012/0053354 A1    Mar. 1, 2012

(30) Foreign Application Priority Data
Feb. 17, 2009  (JP) .................. 2009-034633

(51) Int. Cl.
*C07D 301/08*    (2006.01)

(52) U.S. Cl.
USPC ........................................... 549/523

(58) Field of Classification Search
USPC ........................................... 549/523
See application file for complete search history.

(56) References Cited

U.S. PATENT DOCUMENTS

2003/0010622 A1   1/2003   Moran

FOREIGN PATENT DOCUMENTS

| JP | A-H05-294957 | 11/1993 |
| JP | A-2002-193866 | 7/2002 |
| JP | A-2004-285001 | 10/2004 |
| JP | A-2011-042733 | 3/2011 |

OTHER PUBLICATIONS

A. L. Henne, P. Hill, J. Am. Chem. Soc., 65, 752 (1943).
"Shin Jikken Kagaku Koza 15, Sanka to Kangen I-2" ("New Experimental Chemistry Lesson 15, Oxidation and Reduction I-2"), edited by Chemical Society of Japan, Maruzen, 1976, p. 592.
R. Criegee, Angew. Chem. Int. Ed., 14, 745 (1975).
J. K. Stille, R. T. Foster, J. Org. Chem., 28, 2703 (1963).

*Primary Examiner* — Taofiq A Solola
(74) *Attorney, Agent, or Firm* — K. David Crockett, Esq.; Niky Economy Syrengelas, Esq.; Crockett & Crockett, PC

(57) ABSTRACT

[Problem] There is provided a method for producing an oxygen-containing compound safely and with improved reaction efficiency, in which an undesired peroxide is unlikely to be produced, and efficient heat exchange of the ozonization can be achieved.
[Mean for solving the Problem] The method comprises an ozonization reaction step of continuously supplying, together with an organic compound, ozone having an oxygen content of less than 10% in a dissolved state in high-pressure carbon dioxide to an ozonization reaction section having a thin tubular shape, and reacting the ozone and the organic compound under conditions that suppress generation of oxygen due to thermal decomposition of the ozone, thereby continuously producing an ozonide; and a decomposition reaction step of continuously supplying the ozonide produced in the ozonization reaction step to a decomposition reaction section having a thin tubular shape, thereby continuously producing an oxygen-containing compound, the decomposition reaction step being provided in a manner continuous with the ozonization reaction step.

10 Claims, 2 Drawing Sheets

METHOD FOR PRODUCING OXYGEN-CONTAINING COMPOUND

FIELD OF THE INVENTIONS

The present invention relates to a method for producing an oxygen-containing compound, and more particularly to a safe and efficient method for producing an oxygen-containing compound using ozone.

BACKGROUND OF THE INVENTIONS

Oxidation reactions are reactions that are most frequently utilized in the chemical industry from bulk chemicals to fine chemicals, and a number of studies are being conducted on these reactions.

With respect to oxidizing agents used in the oxidation reactions, their raw materials range from the most inexpensive oxygen to nitric acid, hydrogen peroxide, and metal oxides in the order of increasing cost, and these oxidizing agents are used in the production of a variety of useful compounds.

For example, adipic acid, which is a raw material of Nylon 66, is currently produced by a method in which cyclohexanol alone or a mixture of cyclohexanol and cyclohexanone (KA oil) is oxidized with nitric acid. In such nitric acid oxidation, nitrous oxide ($N_2O$) and $NO_x$, which are said to have global-warming potentials at least 300 times higher than that of carbon dioxide, are formed as by-products. Thus, expensive exhaust-gas processing facilities are needed to process these by-products.

In view of this, as a result of focusing on the fact that KA oil is obtained by way of catalytic oxygen oxidation of cyclohexane and studying this catalytic reaction, a method whereby adipic acid is directly obtained from cyclohexane has been developed. Although the use of the most inexpensive molecular oxygen or air is industrially ideal, it has not yet been used for industrial purposes because of its insufficient conversion and selectivity.

Direct oxidation of cyclohexene to adipic acid using hydrogen peroxide solution is also being studied. Although the yield is good, and hydrogen peroxide does not give off any harmful by-products such as in nitric acid oxidation, hydrogen peroxide is far more expensive than nitric acid. Therefore, this method has not yet been used for industrial purposes.

On the other hand, it has been reported that adipic acid can be obtained by ozonizing cyclohexene, followed by treatment with hydrogen peroxide (Non-Patent Literature 1). Ozone can be obtained by, for example, subjecting oxygen to silent discharge, and the ozonization reaction can be conducted without a catalyst because ozone is highly reactive. Ozonolysis is considered to be an excellent oxidation reaction for industrial purposes, such as for the production of adipic acid by ozonolysis of cyclohexene, in view of resources and waste, because a carboxylic acid can be derived by oxygen oxidation or the like, instead of treating an ozonide with hydrogen peroxide.

However, it has been reported that, in the ozonolysis of an organic compound, "the risk of an explosion must always be kept in mind because an organic peroxide is produced" (Non-Patent Literature 2); therefore, the reaction has almost never been conducted on an industrial scale. Even in the reaction on a small scale in a laboratory, isolation and purification of an ozonide produced by ozonization has been considered to be dangerous.

Thus, many studies have been conducted in order to safely handle ozonolysis. Examples of proposed methods include a method in which, during ozonization, a fatty acid is added to a raw material olefin to control the rate of production of an undesired unstable peroxide, and the proportion of the produced peroxide is monitored using NMR, thereby ensuring the safety of oxidation decomposition by oxygen subsequent to the ozonization (Patent Literature 1); a method in which, after the ozonization reaction or reduction treatment of an ozonide using platinum/hydrogen, purification is conducted by steam distillation (Patent Literature 2); and a method in which ozone is contacted in a micro-reactor, thereby efficiently removing the reaction heat due to ozonization (Patent Literature 3).

The ozone gas that has been used in many of these ozonization methods is a mixed gas containing about 3% of ozone and the remaining 97% of oxygen and obtained by an ozone generator using oxygen as a raw material. In the ozonization reaction of double bonds, it is believed that ozone undergoes an addition reaction with double bonds to produce a molozonide, which subsequently undergoes a rearrangement that involves cleavage of carbon-carbon bonds, thus producing a so-called ozonide (Non-Patent Literature 3). It is believed that, during this rearrangement of the molozonide, oxygen present in excess of ozone forms radicals to produce an undesired unstable peroxide, thus making the reaction dangerous and complicated. Stille et al., in practice, conducted a reaction using ozone having a relatively low oxygen content by concentrating ozone by passing a mixed gas of ozone and oxygen, which exited from an ozonizer, through a silica gel to selectively adsorb the ozone, and subsequently desorbing the ozone with nitrogen gas. Consequently, they dramatically reduced side reactions (Non-Patent Literature 4). Ozonolysis in which the influence of oxygen has been reduced by generating ozone by corona discharge under a carbon dioxide stream without using oxygen has also been proposed (Patent Literature 4).

CITATION LIST

Patent Literature

Patent Literature 1: JP-A-H05-294957
Patent Literature 2: JP-A-2002-193866
Patent Literature 3: JP-A-2004-285001
Patent Literature 4: U.S. Pat. No. 2003/0010622 A1

Non-Patent Literature

Non-Patent literature 1: A. L. Henne, P. Hill, *J. Am. Chem. Soc.*, 65, 752 (1943).
Non-Patent literature 2: "*Shin Jikken Kagaku Koza* 15, *Sanka To Kangen I-2*" ("New Experimental Chemistry Lesson 15, Oxidation and Reduction I-2"), edited by Chemical Society of Japan, Maruzen, 1976, p. 592.
Non-Patent literature 3: R. Criegee, *Angew. Chem. Int. Ed.*, 14, 745 (1975).
Non-Patent literature 4: J. K. Stille, R. T. Foster, *J. Org. Chem.*, 28, 2703 (1963).

SUMMARY

Technical Problem

However, the ozonization described in Patent Literatures 1 to 3 is conducted in an environment in which a large amount of oxygen is present; therefore, an undesired peroxide is inevitably easily produced. Thus, sufficient safety measures have not been taken.

Considering that ozonization is estimated to be an exothermic reaction that produces heat as much as 100 kcal/mol (D. Cremer, *Angew. Chem. Int. Ed.*, 20, 888 (1981)), it is easily imaginable that when highly reactive ozone is contacted with a substrate without the use of a solvent, efficient removal of the reaction heat is not easy, posing a risk that the reaction may become uncontrolled. An organic solvent is often used to dissolve an organic compound; however, in the case of an oxidation reaction, it is necessary to use a solvent inert to the oxidizing agent, in order to safely conduct the reaction.

In the methods described in Non-Patent Literature 4 and Patent Literature 4 that use ozone having a reduced oxygen content during ozonization, the risk has been significantly reduced; however, in both of these methods, the reaction is conducted in an organic solvent reactive to ozone. In view of the possibility of any unexpected events, the use of a flammable organic solvent is desirably avoided.

Moreover, in conventional ozonization, the reaction has been conducted by bubbling an ozone-containing gas into a solution containing an organic compound. However, the solubility of the gas in the solution is limited, and, hence, this ozonization reaction is a reaction in which the dissolution of the ozone gas is rate-limiting, thus requiring a long time until the reaction is completed.

When the ozonization reaction requires a long time, the highly reactive ozonide produced is also present in the reaction solution for a long time, thus easily causing an undesired unstable peroxide to be produced. Such a long ozonization reaction also causes thermal decomposition of ozone to proceed, causing the problem of oxygen production, and an increased risk of an explosion.

Accordingly, an object of the present invention is to provide a method for producing an oxygen-containing compound safely and with improved reaction efficiency, in which an undesired peroxide is unlikely to be produced, and efficient heat exchange of ozonization can be achieved.

Other objects of the invention will become apparent from the following description.

Solution to Problem

The foregoing objects will be solved by each of the inventions set forth below.

The invention as defined in claim 1 is a method for producing an oxygen-containing compound comprising an ozonization reaction step of continuously supplying, together with an organic compound, ozone having an oxygen content of less than 10% in a dissolved state in high-pressure carbon dioxide to an ozonization reaction section having a thin tubular shape, and reacting the ozone and the organic compound under conditions that suppress generation of oxygen due to thermal decomposition of the ozone, thereby continuously producing an ozonide; and a decomposition reaction step of continuously supplying the ozonide produced in the ozonization reaction step to a decomposition reaction section having a thin tubular shape, thereby continuously producing an oxygen-containing compound, the decomposition reaction step being provided in a manner continuous with the ozonization reaction step.

The invention as defined in claim 2 is the method for producing an oxygen-containing compound according to claim 1, wherein the ozonization reaction section having a thin tubular shape is formed of a thin tube having a tube diameter of 1.0 mm to 30 mm that may include a curved shape.

The invention as defined in claim 3 is the method for producing an oxygen-containing compound according to claim 2, wherein the conditions that suppress generation of oxygen due to thermal decomposition of the ozone include adjusting the flow rate of a fluid containing the ozone, the organic compound, and the high-pressure carbon dioxide supplied to the ozonization reaction section to the range from 0.5 mL/min to 10.0 mL/min.

The invention as defined in claim 4 is the method for producing an oxygen-containing compound according to any of claims 1 to 3, wherein the conditions that suppress generation of oxygen due to thermal decomposition of the ozone include adjusting the concentration of the ozone in the ozonization reaction section to the range from 0.01 M to 0.5 M.

The invention as defined in claim 5 is the method for producing an oxygen-containing compound according to any of claims 1 to 4, wherein a temperature and time at which the residual ratio of ozone at each temperature is 90% or more in a correlation diagram showing change over time in thermal decomposition of ozone in high-pressure carbon dioxide at various temperatures is set as a temperature and reaction time of the ozonization reaction section.

The invention as defined in claim 6 is the method for producing an oxygen-containing compound according to any of claims 1 to 5, wherein the organic compound is a terminal olefin, a cyclic olefin, or an internal olefin.

The invention as defined in claim 7 is the method for producing an oxygen-containing compound according to claim 6, wherein the terminal olefin is represented by formula (1):

Formula (1):

[Chem. 1]

wherein $R^1$ and $R^2$ are the same or different and each represent a hydrogen atom, a halogen atom, a carboxyl group, an alkoxycarbonyl group, an aldehyde group, a $C_1$-$C_{30}$ alkyl group, a $C_1$-$C_4$ alkoxy group, a $C_2$-$C_5$ acyl group, a cycloalkyl group, or an aryl group, and these alkyl chains may be substituted with a $C_1$-$C_4$ alkoxy group, a $C_5$-$C_7$ cycloalkyl group, an aryl group, an aralkyl group, a carboxyl group, an alkoxycarbonyl group, an aldehyde group, a $C_2$-$C_5$ acyl group, a hydroxyl group, a mercapto group, or a halogen atom; and $R^1$ and $R^2$ may also be taken together to represent a 5- to 7-membered cycloalkyl group or heterocycle, such a cycloalkyl group or heterocycle may have fused thereto an additional 3- to 7-membered cycloalkyl or heterocycle, and these alkyl chains may each independently be substituted with a $C_1$-$C_4$ alkyl group, a $C_1$-$C_4$ alkoxy group, a $C_5$-$C_7$ cycloalkyl group, an aryl group, an aralkyl group, a carboxyl group, an alkoxycarbonyl group, an aldehyde group, a $C_2$-$C_5$ acyl group, a hydroxyl group, a mercapto group, or a halogen atom.

The invention as defined in claim 8 is the method for producing an oxygen-containing compound according to claim 6, wherein the cyclic olefin is represented by formula (2):

Formula (2):

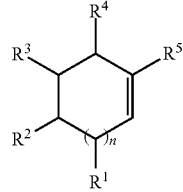

[Chem. 2]

wherein n represents an integer from 0 to 3; $R^1$, $R^2$, $R^3$, $R^4$, and $R^5$ are the same or different and each represent a hydrogen atom, a halogen atom, a hydroxyl group, a carbonyl group, a carboxyl group, an alkoxycarbonyl group, an aldehyde group, an imido group, a $C_1$-$C_4$ alkyl or alkenyl group, a $C_1$-$C_4$ alkoxy group, a $C_2$-$C_5$ acyl group, or a 3- to 7-membered cycloalkyl group or heterocycle, an aryl group or an acid anhydride formed by adjacent ones of $R^1$ to $R^5$ when taken together, or a product formed by crosslinking $R^1$ and $R^4$, $R^1$ and $R^3$, or $R^2$ and $R^4$ at a $C_1$-$C_3$ carbon chain, and these alkyl chains may each independently be substituted with a $C_1$-$C_4$ alkyl group, a $C_1$-$C_4$ alkoxy group, a $C_5$-$C_7$ cycloalkyl group, an aryl group, an aralkyl group, a carboxyl group, an alkoxycarbonyl group, an aldehyde group, a $C_2$-$C_5$ acyl group, a hydroxyl group, a mercapto group, or a halogen atom.

The invention as defined in claim 9 is the method for producing an oxygen-containing compound according to claim 6, wherein the internal olefin is an unsaturated alcohol such as citronellol or phytol, an unsaturated aldehyde such as citronellal, an unsaturated carboxylic acid such as oleic acid or chrysanthemic acid or an ester thereof, natural rubber, or polyisoprene.

The invention as defined in claim 10 is the method for producing an oxygen-containing compound according to any of claims 1 to 5, wherein the organic compound is β-pinene, and the oxygen-containing compound is nopinone.

Another new method for producing an oxygen-containing compound according to any of the preceeding paragraphs, wherein the organic compound is 3-methylene-4H-hexahydrofuro[2,3-b]furan, and the oxygen-containing compound is 4H-hexahydrofuro[2,3-b]furan-3-one.

Advantageous Effects of Invention

In accordance with the present invention, there is provided a method for producing an oxygen-containing compound safely and with improved reaction efficiency, in which an undesired peroxide is unlikely to be produced, and efficient heat exchange of ozonization can be achieved.

REFERENCE SIGNS LIST

Figure 1:
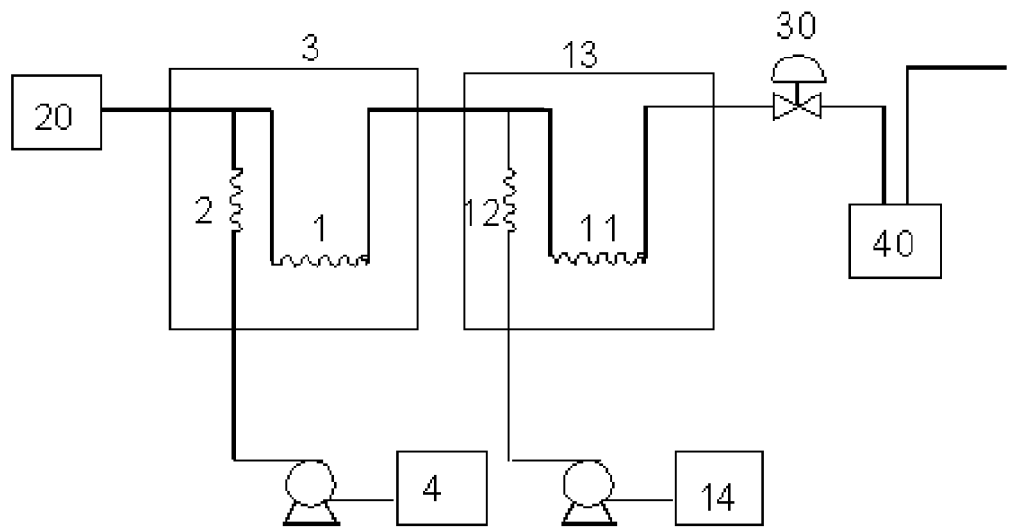
FIG. 1 is a schematic diagram showing one example of an apparatus for performing the method for producing an oxygen-containing compound according to the present invention.

1: ozonization reaction section
2: raw-material preheating tube
3: ozonization reaction vessel
4: raw-material tank
11: decomposition reaction section
12: decomposer preheating tube
13: decomposition reaction vessel
14: decomposer tank
20: supply device for supplying ozone and high-pressure carbon dioxide
30: pressure-regulating valve
40: gas-liquid separation device

DETAILED DESCRIPTION OF THE INVENTIONS

Embodiments of the invention will be described below.
(Ozonization Reaction Step)
Ozone used in the present invention has an oxygen content in the ozone of less than 10%, preferably 5% or less, and more preferably 1% or less. If the ozone has an oxygen content of 10% or more, the probability of the production of an undesired peroxide in an ozonization reaction step increases, making the reaction dangerous.

The ozone used in the present invention can be produced using a general ozone generator.

Many ozone generators generate ozone by causing a discharge in oxygen or an oxygen-containing gas such as air. Unlike ozone used for cleaning or sterilization, ozone not containing oxygen or nitrogen oxide that causes a side reaction is required as the ozone used for the ozonolysis of an organic compound, in order to prevent the production of an undesired peroxide. Thus, pure oxygen is preferably used as an ozonizer.

A gas produced by an ozone generator using oxygen contains several % of ozone and oxygen as the remainder. Therefore, when this gas is used, it needs to be treated so that the oxygen content in the ozone becomes less than 10%.

One example of a known method for obtaining ozone having a reduced oxygen content is a method in which a mixed gas of ozone and oxygen, which is produced by an ozone generator using oxygen as a raw material, is passed through an ozone adsorbent such as a silica gel to selectively adsorb the ozone, thereby concentrating the ozone. However, the resulting concentrated ozone typically has a purity of less than 60% (with an oxygen content of 40% or more), and hence, a purity of 90% or more (with an oxygen content of less than 10%) is difficult to achieve. As described in, for example, a patent document (US Pat 2007 0062372 A1 (Mar. 22, 2007)), when the thus-concentrated ozone is dissolved in liquefied carbon dioxide to prepare a high-pressure carbon dioxide solution of the concentrated ozone, which is subjected to reaction, the production of an explosive peroxide is not sufficiently suppressed.

In contrast, a high-pressure carbon dioxide solution in which ozone having a purity of 99% or more is dissolved can be prepared by, for example, purifying ozone utilizing the difference in boiling point between oxygen and ozone to obtain pure ozone, adsorbing the pure ozone on a silica gel, and subsequently dissolving the ozone in liquefied carbon dioxide. By using such a high-pressure carbon dioxide solution of high-purity ozone, the production of an explosive peroxide is sufficiently suppressed.

The present inventor conducted tests by gasifying each of the above-described high-pressure carbon dioxide solution of concentrated ozone and the above-described high-pressure carbon dioxide solution of high-purity ozone, and by bubbling each of the gasified products into tetrahydrofuran. Consequently, they have ascertained that, when the high-pressure carbon dioxide solution of concentrated ozone is used, a peroxide with a yield of several ten % is produced, whereas when the high-pressure carbon dioxide solution of high-purity ozone is used, substantially no peroxide is produced.

Figure 2:
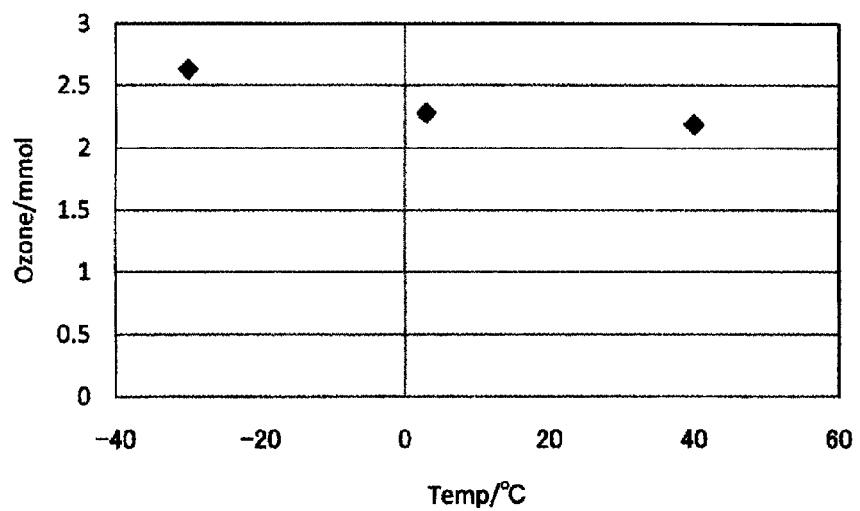
FIG. 2 is a graph showing a relation between the desorption temperature and the dissolved amount of adsorbed ozone.

As shown in FIG. 2, when the ozone adsorbed on an ozone adsorbent is desorbed with liquefied carbon dioxide, a greater amount of the ozone can be dissolved at a lower temperature. Therefore, the desorption temperature is preferably −60° C. to −30° C.

In the present invention, the above-described ozone is continuously supplied, in a dissolved state in high-pressure carbon dioxide, to an ozonization reaction section together with an organic compound.

The term "high-pressure carbon dioxide", as used herein, denotes carbon dioxide in a liquid state having a pressure within 3 to 30 MPa or carbon dioxide in a supercritical state.

In the present invention, because the high-pressure carbon dioxide not only freely mixes with the ozone, but also dissolves the organic compound, it functions as a good reaction solvent for both reaction substrates of the ozone and organic compound. In the present invention, the organic compound, which is present in the high-pressure carbon dioxide in a suspended state without dissolving therein, can also be a reaction substrate.

Consequently, as compared to the method that involves bubbling of an ozone-containing gas in which the dissolution rate of the ozone into the reaction solution is rate-limiting, the ozonization reaction using the high-pressure carbon dioxide solution of high-purity ozone is an extremely efficient reaction, allowing an improved reaction yield (conversion) and a shortened reaction time.

Moreover, the shortened ozonization reaction time allows the production of oxygen due to the thermal decomposition of ozone to be suppressed, and allows the produced highly reactive ozonide to be immediately subjected to a decomposition reaction before any undesired unstable peroxide is produced, thus providing a safer process for producing an oxygen-containing compound.

Furthermore, the high-pressure carbon dioxide has a function called the "radical cage effect", in which carbon dioxide surrounds radicals to thereby make a radical chain reaction unlikely. Therefore, because the production of an undesired peroxide due to radicals is suppressed in the high-pressure carbon dioxide, carbon dioxide plays an important role in constructing a safe ozonolysis reaction, while also having nonflammability.

In the present invention, among organic compounds that are continuously supplied to the ozonization reaction section together with the high-pressure carbon dioxide solution in which ozone having an oxygen content of less than 10%, preferably 5% or less, and more preferably 1% or less, is dissolved, when liquid organic compounds are used, they may be supplied in their undiluted forms, but may also be supplied in a previously dissolved state in the high-pressure carbon dioxide. This promotes counter diffusion between the ozone and organic compound in the ozonization reaction section, thereby further enhancing the efficiency of the ozonization reaction. Among organic compounds supplied to the ozonization reaction section, when solid or gel organic compounds, which have low solubility in the high-pressure carbon dioxide, are used, acetone, acetic acid, or the like having low reactivity with radicals can also be used as an entrainer of the high-pressure carbon dioxide.

The method for producing an oxygen-containing compound according to the present invention is conducted as a continuous reaction using a thin tube, in which the ozone and organic compound are continuously supplied to the ozonization reaction section that includes the thin tube.

One feature of the ozonization reaction step of the present invention is that the reaction is conducted under conditions that suppress generation of oxygen due to the thermal decomposition of ozone.

That is, in the ozonization reaction step, the generation of oxygen due to the thermal decomposition of ozone increases the probability of the production of an undesired unstable peroxide, leading to an increased risk of an explosion and the like. However, in the present invention, this risk is eliminated because the reaction is conducted under conditions that suppress generation of oxygen due to the thermal decomposition of ozone. The structure of the ozonization reaction step for suitably forming the conditions that suppress generation of oxygen due to the thermal decomposition of ozone will hereinafter be described.

First, the ozonization reaction section of the present invention has a thin tubular shape, which preferably has a tube diameter of 1.0 mm to 30 mm. This enables efficient removal of a large amount of reaction heat generated by the ozonization reaction. The thin tube that forms the above-described ozonization reaction section preferably has a shape for increasing the efficiency of mixing the reactants, for example, a curved shape such as a coil shape. In order to increase the mixing efficiency, a static mixer can also be used.

When the tube diameter is 1.0 mm to 30 mm, the flow rate of a fluid containing the ozone, organic compound, and high-pressure carbon dioxide in the ozonization reaction section is preferably 0.5 mL/min to 10.0 mL/min. Within this range, the effect of stirring the components in the fluid owing to the flow rate can be sufficiently obtained in the reaction section, causing the reaction heat to be dispersed, thereby preventing generation of oxygen due to the thermal decomposition of the ozone.

The ozone concentration in the high-pressure carbon dioxide supplied to the ozonization reaction section is set in the range from 0.01 M to 0.5 M. When the substrate concentration is thus set to be low to lower the reaction density, the reaction heat is dispersed. Therefore, the production of oxygen due to the thermal decomposition of ozone is prevented, and the high-pressure carbon dioxide inhibits the progress of a radical reaction, so as to also prevent the formation of an undesired peroxide. The concentration of the organic compound in the high-pressure carbon dioxide supplied to the ozonization reaction section is also preferably set in the range from 0.01 M to 0.5 M.

The temperature of the ozonization reaction section may depend on the reactivity of the organic compound used, but the reaction is typically conducted at −30° C. to 150° C., and preferably at 0° C. to 100° C.

Figure 3:
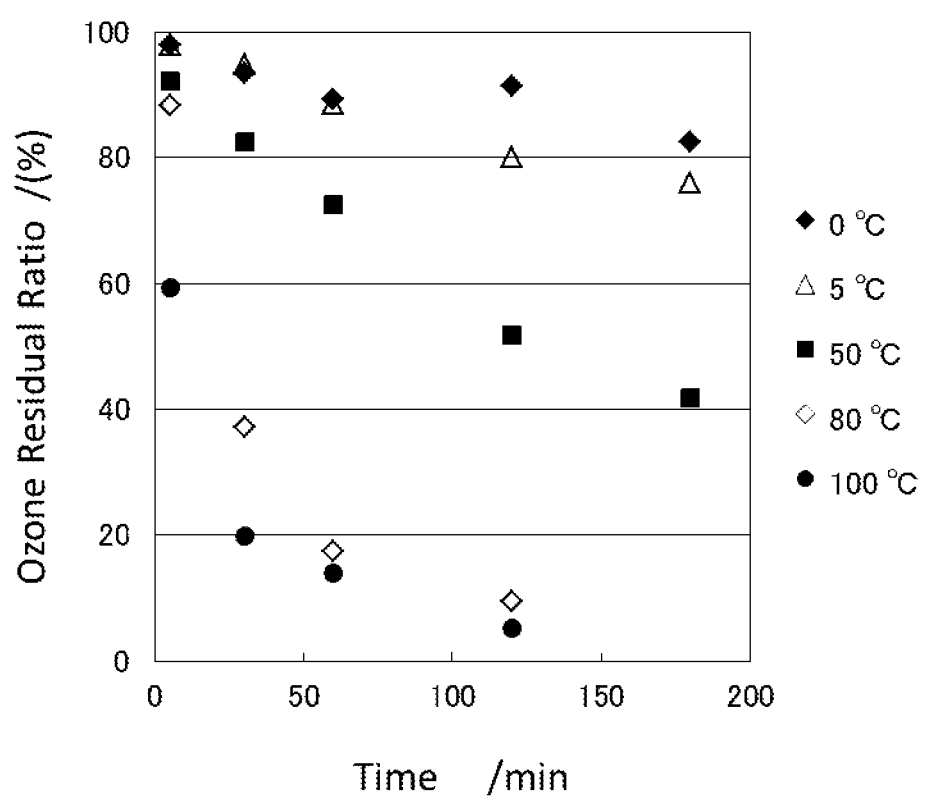
FIG. 3 is a graph showing a relation between the time and the residual ratio of ozone in high-pressure carbon dioxide at various temperatures.

Moreover, because ozone undergoes gradual decomposition even in the high-pressure carbon dioxide, a correlation diagram as shown in FIG. 3 showing change over time in the thermal decomposition of ozone in high-pressure carbon dioxide at various temperatures can be used for reference when determining the reaction temperature and time of the ozonization reaction.

In the present invention, it is preferable that the temperature and time at which the residual ratio of ozone at each temperature is 90% or more in the above-mentioned correlation diagram be set as the temperature and reaction time of the ozonization reaction section.

If the reaction time is long, the produced ozonide may undergo abnormal decomposition, or may begin to significantly increase in amount, causing the yield to decrease. It is thus necessary to adopt a minimum required reaction time. The reaction time may depend on the reactivity and reaction temperature of the organic compound used, but is preferably 0.1 second to 30 minutes. Similarly, the transit time from the ozonization reaction to the subsequent ozonide decomposition reaction is desirably as short as possible.

In the ozonization reaction step, preferred examples of organic compounds supplied to the ozonization reaction section include terminal olefins, cyclic olefins, and internal olefins.

Among the organic compounds of the present invention, examples of terminal olefins include those represented by formula (1) shown above. Specific examples include 1-butene, 1-hexene, 1-octene, 1-decene, 1-dodecene, 1-octadecene, 2-methyl-1-butene, 2-ethyl-1-butene, 2-methyl-1-hexene, 2-ethyl-1-hexene, 2-methyl-1-octene, 2-ethyl-1-octene, 2-methyl-1-decene, 2-ethyl-1-decene, 2-methyl-1-dodecene, 2-ethyl-1-dodecene, 2-methyl-1-octadecene, 2-ethyl-1-octadecene, β-pinene, camphene, sabinene, isophytol, 3-methylene-4H-hexahydrofuro[2,3-b]furan, longifolene, 5-hexenyldichlorosilane, and 5-hexenylmethyldimethoxysilane. Preferred examples include β-pinene, camphene, sabinene, isophytol, 3-methylene-4H-hexahydrofuro[2,3-b]furan, decene, and octadecene.

Among the organic compounds of the present invention, examples of cyclic olefins include those represented by formula (2) shown above. Specific examples include cyclopentene, cyclohexene, cycloheptene, cyclooctene, cyclodecene, cyclododecene, 1-methylcyclopentene, 3-methylcyclopentene, 4-methylcyclopentene, 1,3-dimethylcyclopentene, 1,4-dimethylcyclopentene, 1,5-dimethylcyclopentene, 3,4-dimethylcyclopentene, 3,5-dimethylcyclopentene, 1,3,4-trimethylcyclopentene, 1,3,5-trimethylcyclopentene, 1,4,5-trimethylcyclopentene, 3,4,5-trimethylcyclopentene, 1,3,4,5-tetramethylcyclopentene, 1-methylcyclohexene, 3-methylcyclohexene, 4-methylcyclohexene, 1,3-dimethylcyclohexene, 1,4-dimethylcyclohexene, 1,5-dimethylcyclohexene, 1,6-dimethylcyclohexene, 3,4-dimethylcyclohexene, 4,5-dimethylcyclohexene, 3,5-dimethylcyclohexene, 1,3,4-trimethylcyclohexene, 1,3,5-trimethylcyclohexene, 1,3,6-trimethylcyclohexene, 1,4,5-trimethylcyclohexene, 1,4,6-trimethylcyclohexene, 1,5,6-trimethylcyclohexene, 3,4,5-trimethylcyclohexene, 3,4,6-trimethylcyclohexene, 1,3,4,5-tetramethylcyclohexene, 1,3,4,6-tetramethylcyclohexene, 1,3,5,6-tetramethylcyclohexene, 1,4,5,6-tetramethylcyclohexene, 3,4,5,6-tetramethylcyclohexene, 1,3,4,5,6-pentamethylcyclohexene, 1-methylcycloheptene, 1-methylcyclooctene, 1-chlorocyclopentene, 1-bromocyclopentene, 1-chlorocyclohexene, 1-bromocyclohexene, cyclopentene-1-carboxylic acid, cyclohexene-1-carboxylic acid, 1-acetylcyclopentene, 1-acetylcyclohexene, 1,5-cyclooctadiene, 3-carene, limonene, α-pinene, norbornene, tetracyclo[6.2.1.1(3,6).0(2,7)]dodeca-4,9-diene, bicyclo(2.2.1)hept-5-ene-2,3-endo-dicarboxylic anhydride, cyclohexene-4,5-dicarboxylic anhydride, cyclohexene-cis-4,5-dicarboxylic acid, acenaphthylene, phenanthrene, 2-methylphenanthrene, and 4H-cyclopenta[def]phenanthrene. Preferred examples include cyclohexene, cyclopentene, cyclooctene, cyclodecene, cyclododecene, 3-carene, limonene, α-pinene, cyclohexene-4,5-dicarboxylic acid, and cyclohexene-4,5-dicarboxylic anhydride.

Examples of internal olefins among the organic compounds of the present invention include unsaturated alcohols such as citronellol, nerol, and phytol; unsaturated aldehydes such as citronellal; unsaturated fatty acids such as oleic acid, linolic acid, linolenic acid, fumaric acid, maleic acid, chrysanthemic acid, and citronellic acid, as well as esters thereof; and 2-phenyl heptafluoroisobutenyl ether. Further examples include polybutadiene, natural rubber, homopolymers of polyisoprene, polychloroprene, and the like, and copolymers thereof.

(Decomposition Reaction Step)

The ozonide produced by the ozonization reaction step is continuously supplied to a decomposition reaction step of producing an oxygen-containing compound by decomposition of the ozonide.

The decomposition reaction step of an ozonide include thermal decomposition treatment, oxidative decomposition treatment, and reductive decomposition treatment. In the present invention, these treatments can be suitably selected and used, so as to obtain a desired oxygen-containing compound, as in the selection of a treatment method for a general ozonide decomposition reaction.

Among the above treatments in the decomposition reaction step, the thermal decomposition treatment is the easiest treatment method because it can be conducted without the use of a decomposer. However, due to a concern for an explosion of a highly reactive peroxide by-product, the practical use of the thermal decomposition treatment has previously been considered to be difficult. In the present invention, however, because the production of a highly reactive peroxide is sufficiently suppressed, the thermal decomposition treatment can be conducted safely and easily, and can be used as the most preferred ozonide treatment method.

When the thermal decomposition treatment is performed, the temperature of a decomposition reaction section can be selected, so as to obtain a desired oxygen-containing compound, as in the selection of a temperature of a general ozonide decomposition reaction. The temperature is preferably set from the temperature of the ozonization reaction section to 300° C., and more preferably from 20° C. to 200° C.

When the thermal decomposition treatment is performed, the ozonization reaction section may also function as a decomposition reaction section. That is, the ozonization reaction step and decomposition reaction step can be performed in the single reaction section, allowing the produced ozonide to be decomposed immediately, leading to further improved safety.

In the present invention, when the oxidative decomposition treatment or reductive decomposition treatment is used in the decomposition reaction step, the decomposer may be selected as in the selection of a decomposer for a general ozonide decomposition reaction. Examples of decomposers selected will be described below.

First, the oxidative decomposition treatment is typically performed by contacting the reaction solution with a decomposer, which is an oxidizing agent.

Examples of oxidizing agents include oxygen, alkaline hydrogen peroxide, formic acid, hydrogen peroxide, peracetic acid, silver oxide, chromic acid, and peroxytrifluoroacetic acid. In these cases, a carboxylic acid, a carboxylate ester, or a ketone is obtained as an oxygen-containing compound. Moreover, simple addition of water causes carbonic acid to be produced in carbon dioxide in a liquid or supercritical state, causing a similar reaction. Therefore, water can also be used as a decomposer.

Meanwhile, the reductive decomposition treatment is performed by, for example, contacting the reaction solution with a decomposer, which is a reducing agent.

Examples of reducing agents include sulfide compounds such as dimethylsulfide, diethylsulfide, diphenylsulfide, and β-thiodiglycol; tervalent phosphorus compounds such as triphenyl phosphine, tri-o-tolylphosphine, tri-n-butylphosphine, tricyclohexylphosphine, and phosphite esters; alkali metal sulfites such as sodium sulfite and potassium sulfite; alkali metal iodides such as sodium iodide and potassium iodide; thiourea and glyoxylic acid. In these cases, an aldehyde or a ketone is obtained as an oxygen-containing compound.

Alternatively, the reaction solution may be subjected to reduction treatment with a metal such as, for example, zinc, or the reaction solution may be reacted with hydrogen in the presence of a metal catalyst such as, for example, palladium carbon, platinum, or Raney nickel. Also, in this case, an alcohol, an aldehyde, or a ketone is produced as an oxygen-containing compound.

A metal hydride such as, for example, lithium aluminium hydride or sodium borohydride, is also usable as a reducing agent. In this case, an alcohol is obtained as an oxygen-containing compound.

Preferred examples of the organic compound subjected to the reaction and of the resulting oxygen-containing compound in the present invention will be specifically described.

For example, when β-pinene is subjected to the ozonization reaction step as the organic compound, and the resulting ozonide is thermally decomposed in the decomposition reaction step, nopinone is obtained as an oxygen-containing compound.

For example, when 3-methylene-4H-hexahydrofuro[2,3-b]furan is subjected to the ozonization reaction step as the organic compound, and the resulting ozonide is thermally decomposed in the decomposition reaction step, 4H-hexahydrofuro[2,3-b]furan-3-one is obtained as an oxygen-containing compound.

Nopinone and 4H-hexahydrofuro[2,3-b]furan-3-one noted above are important as raw materials of, for example, pharmaceuticals, but an efficient synthesis method therefore has not heretofore been established. Thus, the effect of the present invention that allows safe and efficient production of these compounds is significant.

(Continuous Reaction Apparatus)

FIG. 1 is a schematic diagram showing one example of an apparatus for performing the above-described method for producing an oxygen-containing compound according to the present invention.

In the continuous reaction apparatus shown in FIG. 1, a supply device 20 for supplying ozone and high-pressure carbon dioxide includes an ozone-generating device, a pure ozone-producing device, a carbon dioxide supply device, a mixing device for ozone/high-pressure carbon dioxide, pumps, and the like. The supply device 20 for supplying ozone and high-pressure carbon dioxide is configured to allow the supply of a high-pressure carbon dioxide solution in which ozone having an oxygen content of less than 10%, preferably 5% or less, and more preferably 1% or less, is dissolved.

Reference sign 1 denotes an ozonization reaction section formed of a coil-shaped thin tube, and reference sign 11 denotes a decomposition reaction section formed of a coil-shaped thin tube. The ozonization reaction section 1 is preferably formed of a thin tube having a tube diameter of 1.0 mm to 30 mm that may include a curved shape. A static mixer may also be provided to increase the mixing efficiency.

Reference sign 30 denotes a pressure-regulating valve for controlling the pressure in the ozonization reaction section 1 and decomposition reaction section 11, which are provided in a continuous manner.

The supply device 20 for supplying ozone and high-pressure carbon dioxide, ozonization reaction section 1, decomposition reaction section 11, and pressure-regulating valve 30 are disposed in a continuous manner so that an oxygen-containing compound can be continuously produced by a continuous ozonization reaction and a subsequent continuous decomposition reaction.

An ozonization reaction vessel 3 that accommodates the ozonization reaction section 1 adjusts the temperature of the ozonization reaction section. Similarly, a decomposition reaction vessel 13 that accommodates the decomposition reaction section 11 adjusts the temperature of the decomposition reaction section 11.

Reference sign 4 denotes a reaction-material tank for storing an organic compound used as a raw material. The organic compound is pumped from the raw-material tank 4 into a raw-material preheating tube 2 where it is preheated to a reaction temperature. The organic compound is then combined with the high-pressure carbon dioxide solution of ozone delivered from the ozone supply device 20, and the mixture is supplied to the ozonization reaction section 1 where the ozonization reaction takes place. Preferably, the organic compound from the raw-material tank 4 is supplied to the ozonization reaction section after it has been dissolved in high-pressure carbon dioxide beforehand, by providing a high-pressure carbon dioxide supply device not illustrated.

Meanwhile, reference sign 14 denotes a decomposer tank. The decomposer is pumped from the decomposer tank 14 into a decomposer preheating tube 12 where it is preheated to a reaction temperature and then combined with an ozonization reaction mixture containing an ozonide, which is continuously supplied from the ozonization reaction vessel 13, whereby a decomposition reaction takes place. When the thermal decomposition treatment described above is conducted in the decomposition reaction step, these supply means for supplying a decomposer can be omitted. Further, as described above, when the ozonization reaction section also functions as a decomposition reaction section, the decomposition reaction section 11, decomposer preheating tube 12, decomposition reaction vessel 13, and decomposer tank 14 can be omitted.

A decomposition reaction mixture containing an oxygen-containing compound continuously leaked through the pressure-regulating valve 30 is introduced into a gas-liquid separation device 40, where the high-pressure carbon dioxide is gasified and separated from the product. In the gas-liquid separation device 40, a vessel containing a decomposer may be placed, and an additional decomposition reaction may be conducted while bubbling, or a vessel for trapping the product may be placed to collect the product. The gasified carbon dioxide can be liquefied and returned into the ozone supply device for recycling.

A pump of the supply device 20 for supplying ozone and high-pressure carbon dioxide, pumps disposed in the raw-material tank 4 in a continuous manner, and the pressure-regulating valve 30 are provided so that they can regulate the flow rate of the fluid containing the ozone, organic compound, and high-pressure carbon dioxide supplied to the ozonization reaction section 1.

As described above, when the ozonization reaction section 1 is formed of a thin tube having a tube diameter of the range from 1.0 mm to 30 mm, the flow rate of the fluid containing the ozone, organic compound, and high-pressure carbon dioxide supplied to the ozonization reaction section 1 is preferably adjusted in the range from 0.5 mL/min to 10.0 mL/min.

The pump of the supply device 20 for supplying ozone and high-pressure carbon dioxide, the pumps disposed in the raw-material tank 4 in a continuous manner, and the pressure-regulating valve 30 are also provided so that they can adjust the concentration of each of the ozone and organic compound in the ozonization reaction section 1. Preferably, the concentration of each of the ozone and organic compound in the ozonization reaction section 1 is adjusted in the range from 0.01 M to 0.5 M.

As described above, it is preferable that the temperature and time at which the residual ratio of ozone at each temperature is 90% or more in the correlation diagram (FIG. 3) showing change over time in the thermal decomposition of ozone in high-pressure carbon dioxide at various temperatures be set as the temperature and reaction time of the ozonization reaction section 1. Temperature control and reaction time control by setting the flow rate, tube diameter, and the length of the thin tube in the ozonization reaction vessel 3 are conducted so as to match the set temperature and reaction time of the ozonization reaction section 1

The amount of oxygen-containing compound produced can be easily increased by disposing in parallel an increased number of thin tubes to be reacted.

By using this continuous reaction apparatus, the above-described method for producing an oxygen-containing compound according to the present invention, i.e., a method for producing an oxygen-containing compound safely and with improved reaction efficiency, in which the generation of oxygen due to the thermal decomposition of ozone is suppressed, an undesired peroxide is unlikely to be produced, and efficient heat exchange of ozonization can be achieved, can be performed.

(Batch Reaction)

While the method and apparatus for continuously producing an oxygen-containing compound have been described above, an invention for producing an oxygen-containing compound by a batch reaction using a pressure vessel such as an autoclave will be described below.

In the case of a batch reaction using a pressure vessel such as an autoclave, high-pressure carbon dioxide in which ozone having an oxygen content of less than 10%, preferably 5% or less, and more preferably 1% or less, is dissolved, and an organic compound are supplied into the pressure vessel, and then an ozonization reaction is conducted at a set pressure of 3 to 30 MPa inside the pressure vessel.

During the ozonization reaction, the ozone concentration in the high-pressure carbon dioxide inside the pressure vessel is preferably adjusted in the range from 0.01 M to 0.5 M. When the substrate concentration is thus set to be low to lower the reaction density, the reaction heat is dispersed. Therefore, the production of oxygen due to the thermal decomposition of ozone is prevented, and the high-pressure carbon dioxide inhibits the progress of a radical reaction, so as to also prevent the formation of an undesired peroxide. The concentration of the organic compound in the high-pressure carbon dioxide supplied to an ozonization reaction section is also preferably set in the range from 0.01 M to 0.5 M.

As described above, it is preferable that the temperature and time at which the residual ratio of ozone at each temperature is 90% or more in the correlation diagram (FIG. 3) showing change over time in the thermal decomposition of ozone in high-pressure carbon dioxide at various temperatures be set as the temperature inside the pressure vessel and reaction time.

The ozonization reaction is preferably conducted while stirring using a stirring means provided inside the pressure vessel. This causes dispersion of the reaction heat produced by the ozonization reaction, further suppressing the production of oxygen due to the thermal decomposition of ozone.

Carbon dioxide is supplied by, for example, replacing the inside of the pressure vessel with carbon dioxide gas, and by further adding liquefied carbon dioxide thereto. Here, the internal pressure can be adjusted to 3 to 30 MPa by heating the pressure vessel, thereby causing the liquefied carbon dioxide to undergo a phase transition.

After the ozonization reaction, an oxygen-containing compound can be obtained by subjecting the produced ozonide to any of the thermal decomposition treatment, oxidative decomposition treatment, and reductive decomposition treatment. The decomposition reaction may be conducted with the ozonide being maintained inside the pressure vessel, or may be conducted after removing the ozonide from the pressure vessel by extraction or the like.

By using this batch reaction apparatus, the method for producing an oxygen-containing compound safely and with improved reaction efficiency, in which the generation of oxygen due to the thermal decomposition of ozone is suppressed, and an undesired peroxide is unlikely to be produced, can be performed.

Note that the detailed description of the invention of a continuous reaction described above can be referred to for a more detailed description of the invention of a batch reaction described above.

EXAMPLES

Effects of the invention will be demonstrated below with reference to examples; however, the invention is not limited to these examples.

Reference Example 1

Pure ozone (prepared in accordance with *Rev. Sci. Instrum.* 1989, 60, 3769) was adsorbed to saturation at −60° C. on a silica gel placed in a stainless steel vessel, and high-pressure carbon dioxide was passed through the stainless steel vessel at the same temperature, thereby preparing a high-pressure carbon dioxide solution of ozone.

Reference Example 2

An ozone/oxygen gas obtained from an ozonizer containing several % of ozone was adsorbed to saturation at −60° C. on a silica gel placed in a stainless steel vessel, and high-pressure carbon dioxide was passed through the stainless steel vessel, thereby preparing a high-pressure carbon dioxide solution of ozone.

Measurement Method

1. Purity Analysis of Ozone
1-1 Quantification of the Amount of Ozone
In Reference Example 1 or 2, Ar gas cooled to −60° C. was passed through the stainless steel vessel containing the silica gel on which the ozone was adsorbed to saturation at −60° C., before the addition of high-pressure carbon dioxide, and the desorbed gas was passed through a KI aqueous solution. The amount of iodine produced was titrated with a sodium thiosulfate solution, and the amount of ozone was quantified.
1-2 Quantification of the Total Amount of Ozone and Oxygen
The gas desorbed through Ar gas in the same manner as in the quantification of the amount of ozone shown in 1-1 was passed through reduced copper heated to 350° C., and the total amount of ozone and oxygen was quantified based on the amount of a weight increase.
1-3 Ozone Purity
The purity of the ozone was determined in terms of percentage of the amount of ozone (1-1) relative to the total amount of ozone and oxygen (1-2).
2. Quantitative Analysis of Peroxide
The valve of the stainless steel vessel containing the high-pressure carbon dioxide solution of high-purity ozone obtained in Reference Example 1, or the valve of the stainless steel vessel containing the high-pressure carbon dioxide solution of concentrated ozone obtained in Reference Example 2 was opened, and the high-pressure carbon dioxide solution was bubbled into tetrahydrofuran (30 mL) at 5° C. for 20 minutes, so as to supply 0.3 mmol of ozone thereto.

The resulting product was analyzed by NMR measurement.

Results

1. Purity Analysis of Ozone
As a result of the purity analysis, high-purity ozone with a purity of 99% or more (with an oxygen content of less than 1%) was confirmed in Reference Example 1. On the other hand, in Reference Example 2, the ozone purity was from 21 to 56% (with an oxygen content of 79 to 44%), and varied depending on the temperature or flow rate during adsorption on the silica gel.

2. Quantitative Analysis of Peroxide

As a result of the quantitative analysis of a peroxide, in Reference Example 1, the production of a peroxide (2-hydroperoxytetrahydrofuran) with a yield of less than 1% was confirmed. The same yield was also confirmed by quantifying the peroxide using the KI method. On the other hand, in Reference Example 2, the production of a peroxide (2-hydroperoxytetrahydrofuran) with a yield of 59% was confirmed.

Evaluation

It can be understood that, although the ozone whose concentration has been increased to give an oxygen content of up to 79 to 44% is used as in Reference Example 2, the explosive peroxide is produced at a yield as high as 59%; whereas the use of the ozone having an oxygen content of less than 1% results in the production of substantially no peroxide, as in Reference Example 1.

Example 1

An oxygen-containing compound was produced using a reaction apparatus (a decomposer supply device is not connected) similar to that shown FIG. 3.

First, the pressure of a pressure-regulating valve 30 was set to 10 MPa, and a high-pressure carbon dioxide solution in which 0.061 M of ozone having an oxygen content of less than 1% was dissolved was supplied at a flow rate of 1 mL/min from a supply device 20 for supplying ozone and high-pressure carbon dioxide.

β-pinene was supplied from a raw-material tank 4 using a high-pressure pump, and the raw material was preheated in an ozonization reaction vessel 3 at 20° C. The preheated raw material was then combined with the high-pressure carbon dioxide solution of ozone, and continuous ozonization proceeded in a stainless steel coil-shaped ozonization reaction section 1 having an inside diameter of 1 mm and a length of 25 cm and set to 20° C. The reaction mixture that exited from the ozonization vessel 3 was subsequently subjected to a continuous thermal decomposition reaction in a stainless steel coil-shaped decomposition reaction section 11 having an inside diameter of 1 mm and a length of 25 cm and set to 120° C. The residence time corresponding to the reaction time was 11.5 seconds in the ozonization reaction section and 11.5 seconds in the decomposition reaction section, making a total of 23 seconds. The product was passed via the pressure-regulating valve 30 and was dissolved in acetone placed in a gas-liquid separation device 40. Quantification of the acetone solution by gas chromatography using undecane as an internal standard confirmed that 0.78 mmol of nopinone was produced in 30 minutes.

Example 2

An oxygen-containing compound was produced using a reaction apparatus (a decomposer supply device is not connected) similar to that shown FIG. 3.

The pressure of a pressure-regulating valve 30 was set to 10 MPa, and a high-pressure carbon dioxide solution in which 0.092 M of ozone having an oxygen content of less than 1% was dissolved was supplied at a flow rate of 2 mL/min from a supply device 20 for supplying ozone and high-pressure carbon dioxide.

β-pinene was supplied from a raw-material tank 4 using a high-pressure pump, and the raw material was preheated in an ozonization reaction vessel 3 at 2° C. The preheated raw material was then combined with the high-pressure carbon dioxide solution of ozone, and continuous ozonization proceeded in a stainless steel coil-shaped ozonization reaction section 1 having an inside diameter of 1 mm and a length of 26 cm and set to 2° C. The reaction mixture that exited from the ozonization vessel 3 was subsequently subjected to a continuous thermal decomposition reaction in a stainless steel coil-shaped decomposition reaction section 11 having an inside diameter of 1 mm and a length of 100 cm and set to 150° C. The residence time corresponding to the reaction time was 6 seconds in the ozonization reaction section and 24 seconds in the decomposition reaction section, making a total of 30 seconds. The product was passed via the pressure-regulating valve 30 and was dissolved in acetone placed in a gas-liquid separation device 40. Quantification of the acetone solution by gas chromatography using undecane as an internal standard confirmed that 0.48 mmol of nopinone was produced in 30 minutes.

Example 3

An oxygen-containing compound was produced using a reaction apparatus (a decomposer supply device is not connected) similar to that shown FIG. 3.

The pressure of a pressure-regulating valve 30 was set to 10 MPa, and a high-pressure carbon dioxide solution in which 0.058 M of ozone having an oxygen content of less than 1% was dissolved was supplied at a flow rate of 1 mL/min from a supply device 20 for supplying ozone and high-pressure carbon dioxide.

3-Methylene-4H-hexahydrofuro[2,3-b]furan was supplied from a raw-material tank 4 using a high-pressure pump, and the raw material was preheated in an ozonization reaction vessel 3 at 20° C. The preheated raw material was then combined with the high-pressure carbon dioxide solution of ozone, and continuous ozonization proceeded in a stainless steel coil-shaped ozonization reaction section 1 having an inside diameter of 1 mm and a length of 25 cm and set to 20° C. The reaction mixture that exited from the ozonization vessel 3 was subsequently subjected to a continuous thermal decomposition reaction in a stainless steel coil-shaped decomposition reaction section 11 having an inside diameter of 1 mm and a length of 25 cm and set to 120° C. The residence time corresponding to the reaction time was 11.5 seconds in the ozonization reaction section and 11.5 seconds in the decomposition reaction section, making a total of 23 seconds. The product was passed via the pressure-regulating valve 30 and was dissolved in acetone placed in a gas-liquid separation device 40. Quantification of the acetone solution by FT-NMR using coumarin as an internal standard confirmed that 0.73 mmol of 4H-hexahydrofuro[2,3-b]furan-3-one was produced in 30 minutes.

Example 4

An oxygen-containing compound was produced using a reaction apparatus (a decomposer supply device is not connected) similar to that shown FIG. 3.

The pressure of a pressure-regulating valve 30 was set to 10 MPa, and a high-pressure carbon dioxide solution in which 0.088 M of ozone having an oxygen content of less than 1% was dissolved was supplied at a flow rate of 2 mL/min from a supply device 20 for supplying ozone and high-pressure carbon dioxide.

1-Decene was supplied from a raw-material tank 4 using a high-pressure pump, and the raw material was preheated in an ozonization reaction vessel 3 at 20° C. The preheated raw material was then combined with the high-pressure carbon dioxide solution of ozone, and continuous ozonization proceeded in a stainless steel coil-shaped ozonization reaction section 1 having an inside diameter of 1 mm and a length of 26 cm and set to 20° C. The reaction mixture that exited from the ozonization vessel 3 was subsequently subjected to a continuous thermal decomposition reaction in a stainless steel coil-shaped decomposition reaction section 11 having an inside diameter of 1 mm and a length of 100 cm and set to 200° C. The residence time corresponding to the reaction time was 6 seconds in the ozonization reaction section and 24 seconds in the decomposition reaction section, making a total of 30 seconds. The product was passed via the pressure-regulating valve 30 and was dissolved in acetone placed in a gas-liquid separation device 40. Quantification of the acetone solution by FT-NMR using coumarin as an internal standard confirmed that 0.58 mmol of nonanoic acid and 0.63 mmol of nonanal were produced in 30 minutes.

Example 5

An oxygen-containing compound was produced using a reaction apparatus similar to that shown in FIG. 3, except that the decomposition reaction section 11, decomposer preheating tube 12, decomposition reaction vessel 13, and decomposer tank 14 illustrated were not provided, and that the ozonization reaction section 1 also functioned as a decomposition reaction section.

The pressure of a pressure-regulating valve 30 was set to 10 MPa, and a high-pressure carbon dioxide solution in which 0.088 M of ozone having an oxygen content of less than 1% was dissolved was supplied at a flow rate of 2 mL/min from a supply device 20 for supplying ozone and high-pressure carbon dioxide.

1-Methylcyclohexene was supplied from a raw-material tank 4 using a high-pressure pump, and the raw material was preheated in a reaction vessel 3 at 20° C. The preheated raw material was then combined with the high-pressure carbon dioxide solution of ozone, and continuous ozonization and thermal decomposition reactions proceeded in a stainless steel coil-shaped ozonization reaction section 1 (which also functioned as a decomposition reaction section) having an inside diameter of 1 mm and a length of 26 cm and set to 20° C. The residence time corresponding to the reaction time was about 6 seconds. The product was passed via the pressure-regulating valve 30 and was dissolved in acetone placed in a gas-liquid separation device 40. Quantification of the acetone solution by FT-NMR using coumarin as an internal standard confirmed that 1.35 mmol of 6-oxoheptanoic acid was produced in 30 minutes.

Reference Example 3

An oxygen-containing compound was produced using a batch reaction process.

First, β-pinene (0.272 g, 2.00 mmol) was added to a 50 ml stainless steel autoclave, and 28 g of a high-pressure carbon dioxide solution in which 2.7 mmol of ozone having an oxygen content of less than 1% was dissolved was supplied from an ozone supply device to give 5.8 MPa at 5° C.

After stirring for 10 minutes, the temperature was increased to 140° C. to give 21.0 MPa, and stirring while heating was conducted for 15 minutes.

After the reaction, the autoclave was cooled with ice, and the pressure was reduced; subsequently, the reaction mixture was analyzed by FT-NMR using coumarin as an internal standard. The results confirmed that nopinone was obtained in a yield of 52%.

Reference Example 4

An oxygen-containing compound was produced using a batch reaction process.

First, 1-octadecene (0.510 g, 2.02 mmol) was added to a 50 mL stainless steel autoclave, and 28 g of a high-pressure carbon dioxide solution containing 2.7 mmol of ozone having an oxygen content of less than 1% was supplied from an ozone supply device to give 6.8 MPa at 20° C.

After stirring for 10 minutes, the temperature was increased to 140° C. to give 21.0 MPa, and stirring while heating was conducted for 15 minutes.

After the reaction, the autoclave was cooled with ice, and the pressure was reduced; subsequently, the reaction mixture was analyzed by FT-NMR using coumarin as an internal standard. The results confirmed that heptadecanoic acid was obtained in a yield of 78%, and heptadecanal was obtained in a yield of 21%.

Reference Example 5

An oxygen-containing compound was produced using a batch reaction process.

First, cyclohexene (0.164 g, 2.00 mmol) was added to a 50 mL stainless steel autoclave, and 28 g of a high-pressure carbon dioxide solution containing 2.7 mmol of ozone having an oxygen content of less than 1% was supplied from an ozone supply device to give 6.0 MPa at 15° C.

After stirring for 10 minutes, the temperature was increased to 140° C. to give 22 MPa, and stirring while heating was conducted for 15 minutes.

After the reaction, the autoclave was cooled with ice, and the pressure was reduced; subsequently, the contents were treated with diazomethane, and the reaction mixture was analyzed by gas chromatography using biphenyl as an internal standard. The results confirmed that adipic acid was obtained in a yield of 24%.

Reference Example 6

An oxygen-containing compound was produced using a batch reaction process.

First, cyclohexene (0.166 g, 2.02 mmol) was added to a 50 mL stainless steel autoclave, and 45 g of a high-pressure carbon dioxide solution containing 3.0 mmol of ozone having an oxygen content of less than 1% was supplied from an ozone supply device to give 4.9 MPa at 10° C.

After stirring for 1 minute, the pressure was returned to the ordinary pressure. Oxygen (2.04 g) and liquefied carbon dioxide (8.9 g) were newly added, the temperature was increased to 140° C. to give 10.5 MPa, and the mixture was stirred while heating for 60 minutes.

After the reaction, the autoclave was cooled with ice, and the pressure was reduced; subsequently, the contents were treated with diazomethane, and the reaction mixture was analyzed by gas chromatography using biphenyl as an internal standard. The results confirmed that adipic acid was obtained in a yield of 38%, and 6-oxohexanoic acid was obtained in a yield of 18%.

Reference Example 7

An oxygen-containing compound was produced using a batch reaction process.

First, cyclohexene (0.166 g, 2.02 mmol) was added to a 50 mL stainless steel autoclave, and 30.9 g of a high-pressure carbon dioxide solution containing 2.7 mmol of ozone having an oxygen content of less than 1% was supplied from an ozone supply device to give 6.6 MPa at 25° C.

After stirring for 12.5 minutes, the pressure was returned to the ordinary pressure, triphenyl phosphine (0.655 g) and chloroform (1.0 mL) were newly added, and the mixture was stirred for 2 hours at 25° C.

After the reaction, the autoclave was cooled with ice, and the pressure was reduced; subsequently, the contents were treated with diazomethane, and the reaction mixture was analyzed by gas chromatography using biphenyl as an internal standard. The results confirmed that adipic acid was obtained in a yield of 38%, and 6-oxohexanoic acid was obtained in a yield of 18%. With regard to the products, the reaction mixture was analyzed by FT-NMR using coumarin as an internal standard, and the results confirmed that adipaldehyde was obtained in a yield of 42%, and adipic acid was obtained in a yield of 19%.

Reference Example 8

An oxygen-containing compound was produced using a batch reaction process.

First, phytol (0.592 g, 2.00 mmol) was added to a 50 ml stainless steel autoclave, and 37 g of a high-pressure carbon dioxide solution containing 2.7 mmol of ozone having an oxygen content of less than 1% was supplied from an ozone supply device to give 6.1 MPa at 20° C.

After stirring for 12.5 minutes, the temperature was increased to 140° C. to give 24.9 MPa, and stirring while heating was conducted for 15 minutes.

After the reaction, the autoclave was cooled with ice, and the pressure was reduced; subsequently, the reaction mixture was analyzed by FT-NMR using coumarin as an internal standard. The results confirmed that 6,10,14-trimethylpentadeca-2-one was obtained in a yield of 58%.

Reference Example 9

An oxygen-containing compound was produced using a batch reaction process.

First, 1,1-diphenylethylene (0.367 g, 2.04 mmol) was added to a 50 mL stainless steel autoclave, and 42 g of a high-pressure carbon dioxide solution containing 3.0 mmol of ozone having an oxygen content of less than 1% was supplied from an ozone supply device to give 4.2 MPa at 7° C.

After stirring for 5 minutes, the pressure was returned to the ordinary pressure, and excess ozone was removed. 15.9 g of liquefied carbon dioxide was newly added, the temperature was increased to 140° C. to give 10.5 MPa, and the mixture was stirred while heating for 15 minutes.

After the reaction, the autoclave was cooled with ice, and the pressure was reduced; subsequently, the reaction mixture was analyzed by FT-NMR using coumarin as an internal standard. The results confirmed that diphenyl ketone was obtained in a yield of 82%.

Reference Example 10

An oxygen-containing compound was produced using a batch reaction process.

First, natural rubber (0.073 g, 1.07 mmol) and chloroform (5 mL) were added to a 50 mL stainless steel autoclave, and 32 g of a high-pressure carbon dioxide solution containing 2.0 mmol of ozone having an oxygen content of less than 1% was supplied from an ozone supply device to give 4.0 MPa at 0° C.

After stirring for 1 minute, the pressure was returned to the ordinary pressure. Oxygen (2.18 g) and liquefied carbon dioxide (9.2 g) were newly added, the temperature was increased to 100° C. to give 8.0 MPa, and the mixture was stirred while heating for 60 minutes.

After the reaction, the autoclave was cooled with ice, and the pressure was reduced; subsequently, the reaction mixture was analyzed by FT-NMR using coumarin as an internal standard. The results confirmed that levulinic acid was obtained in a yield of 44%.

Reference Example 11

An oxygen-containing compound was produced using a batch reaction process.

First, oleic acid (0.565 g, 2.00 mmol) was added to a 50 mL stainless steel autoclave, and 28 g of a high-pressure carbon dioxide solution of high-purity ozone containing 2.7 mmol of ozone was supplied from an ozone supply device to give 6.5 MPa at 15° C.

After stirring for 10 minutes, the temperature was increased to 140° C. to give 22 MPa, and stirring while heating was conducted for 15 minutes.

After the reaction, the autoclave was cooled with ice, and the pressure was reduced; subsequently, the contents were treated with diazomethane, and the reaction mixture was analyzed by gas chromatography using biphenyl as an internal standard.

The results confirmed that azelaic acid was obtained in a yield of 64%, and nonanoic acid was obtained in a yield of 35%.

I claim:

1. A method for producing an oxygen-containing compound comprising:
an ozonization reaction step of continuously supplying, together with an organic compound wherein the organic compound is a chain having a terminal or non-terminal olefin bond or cycle olefin, ozone having an oxygen content of less than 10% in a dissolved state in high-pressure carbon dioxide to an ozonization reaction section having a thin tubular shape, and reacting the ozone and the organic compound under conditions that suppress generation of oxygen due to thermal decomposition of the ozone, thereby continuously producing an ozonide; and
a decomposition reaction step of continuously supplying the ozonide produced in the ozonization reaction step to a decomposition reaction section having a thin tubular shape, thereby continuously producing an oxygen-containing compound, the decomposition reaction step being provided in a manner continuous with the ozonization reaction step.

2. The method for producing an oxygen-containing compound according to claim 1, wherein the ozonization reaction section having a thin tubular shape is formed of a thin tube having a tube diameter of 1.0 mm to 30 mm.

3. The method for producing an oxygen-containing compound according to claim 2, wherein the flow rate of a fluid containing the ozone, the organic compound, and the high-pressure carbon dioxide supplied to the ozonization reaction section to the range from 0.5 mL/min to 10.0 mL/min.

4. The method for producing an oxygen-containing compound according to claim 3, wherein the concentration of the ozone in the ozonization reaction section to the range from 0.01 M to 0.5 M.

5. The method for producing an oxygen-containing compound according to claim 3, wherein a temperature and time at which the residual ratio of ozone at each temperature is 90% or more in a correlation diagram showing change over time in thermal decomposition of ozone in high-pressure carbon dioxide at various temperatures is set as a temperature and reaction time of the ozonization reaction section.

6. The method for producing an oxygen-containing compound according to claim 1, wherein the the organic compound which is a chain having the terminal olefin bond is represented by formula (1):

Formula (1)

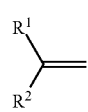

wherein $R^1$ and $R^2$ are the same or different and each represent a hydrogen atom, a halogen atom, a carboxyl group, an alkoxycarbonyl group, an aldehyde group, a $C_1$-$C_{30}$ alkyl group, a $C_1$-$C_4$ alkoxy group, a $C_2$-$C_5$ acyl group, a cycloalkyl group, or an aryl group, and these alkyl chains may be substituted with a $C_1$-$C_4$ alkoxy group, a $C_5$-$C_7$ cycloalkyl group, an aryl group, an aralkyl group, a carboxyl group, an alkoxycarbonyl group, an aldehyde group, a $C_2$-$C_5$ acyl group, a hydroxyl group, a mercapto group, or a halogen atom; and $R^1$ and $R^2$ may also be taken together to represent a 5- to 7-membered cycloalkyl group or heterocycle, such a cycloalkyl group or heterocycle may have fused thereto an additional 3- to 7-membered cycloalkyl or heterocycle, and these alkyl chains may each independently be substituted with a $C_1$-$C_4$ alkyl group, a $C_1$-$C_4$ alkoxy group, a $C_5$-$C_7$ cycloalkyl group, an aryl group, an aralkyl group, a carboxyl group, an alkoxycarbonyl group, an aldehyde group, a $C_2$-$C_5$ acyl group, a hydroxyl group, a mercapto group, or a halogen atom.

7. The method for producing an oxygen-containing compound according to claim 1, wherein the organic compound which is a chain having the cyclic olefin is represented by formula (2):

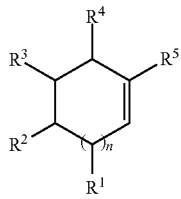

Formula (2)

wherein n represents an integer from 0 to 3; $R^1$, $R^2$, $R^3$, $R^4$, and $R^5$ are the same or different and each represent a hydrogen atom, a halogen atom, a hydroxyl group, a carbonyl group, a carboxyl group, an alkoxycarbonyl group, an aldehyde group, an imido group, a $C_1$-$C_4$ alkyl or alkenyl group, a $C_1$-$C_4$ alkoxy group, a $C_2$-$C_5$ acyl group, or a 3- to 7-membered cycloalkyl group or heterocycle, an aryl group or an acid anhydride formed by adjacent ones of $R^1$ to $R^5$ when taken together, or a product formed by crosslinking $R^1$ and $R^4$, $R^1$ and $R^3$, or $R^2$ and $R^4$ at a $C_1$-$C_2$ carbon chain, and these alkyl chains may each independently be substituted with a $C_1$-$C_4$ alkyl group, a $C_1$-$C_4$ alkoxy group, a $C_5$-$C_7$ cycloalkyl group, an aryl group, an aralkyl group, a carboxyl group, an alkoxycarbonyl group, an aldehyde group, a $C_2$-$C_5$ acyl group, a hydroxyl group, a mercapto group, or a halogen atom.

8. The method for producing an oxygen-containing compound according to claim 1, wherein the organic compound which is a chain having the non-terminal olefin bond is an unsaturated alcohol such as citronellol or phytol, an unsaturated aldehyde such as citronellal, an unsaturated carboxylic acid such as oleic acid or chrysanthemic acid or an ester thereof, natural rubber, or polyisoprene.

9. The method for producing an oxygen-containing compound according to claim 3, wherein the organic compound is β-pinene, and the oxygen-containing compound is nopinone.

10. The method for producing an oxygen-containing compound according to claim 3, wherein the organic compound is 3-methylene-4H-hexahydrofuro[2,3-b]furan, and the oxygen-containing compound is 4H-hexahydrofuro[2,3-b]furan-3-one.

* * * * *